(12) United States Patent
Wozencroft

(10) Patent No.: US 11,071,555 B2
(45) Date of Patent: Jul. 27, 2021

(54) ROTARY CUTTER FOR PREPARING THE ACETABULAR SOCKET FOR A HIP IMPLANT

(71) Applicant: Embody Orthopaedic Limited, London (GB)

(72) Inventor: Robert Wozencroft, Epsom (GB)

(73) Assignee: Embody Orthopaedic Limited, London (GB)

( * ) Notice: Subject to any disclaimer, the term of this patent is extended or adjusted under 35 U.S.C. 154(b) by 82 days.

(21) Appl. No.: 15/774,216

(22) PCT Filed: Nov. 7, 2016

(86) PCT No.: PCT/GB2016/053474
§ 371 (c)(1),
(2) Date: May 7, 2018

(87) PCT Pub. No.: WO2017/077340
PCT Pub. Date: May 11, 2017

(65) Prior Publication Data
US 2019/0083110 A1    Mar. 21, 2019

(30) Foreign Application Priority Data

Nov. 6, 2015 (GB) .................................... 1519624

(51) Int. Cl.
*A61B 17/16* (2006.01)
*A61B 17/88* (2006.01)
*A61B 17/00* (2006.01)

(52) U.S. Cl.
CPC ...... *A61B 17/1666* (2013.01); *A61B 17/1617* (2013.01); *A61B 17/1659* (2013.01);
(Continued)

(58) Field of Classification Search
CPC ............ A61B 17/1666; A61B 17/1659; A61B 17/1617; A61B 17/162; A61B 17/1684; A61B 17/1637; A61B 2017/1602
(Continued)

(56) References Cited

U.S. PATENT DOCUMENTS 4,621,637 A * 11/1986 Fishbein ............ A61B 17/1666
408/227
7,837,686 B1    11/2010 Tulkis
(Continued)

FOREIGN PATENT DOCUMENTS

AU        2016348912        5/2018
CN        200998300         1/2008
(Continued)

OTHER PUBLICATIONS

"International Application Serial No. PCT GB2016 053474, International Preliminary Report on Patentability dated May 17, 2018", 10 pgs.
(Continued)

*Primary Examiner* — Amy R Sipp
(74) *Attorney, Agent, or Firm* — Schwegman Lundberg & Woessner, P.A.

(57) ABSTRACT

A rotary cutter with hemispherical shaped head and a plurality of blades mounted in said head, wherein each of said blades has securement means for securing each blade in position in said head by interacting with an inner surface of said head.

13 Claims, 5 Drawing Sheets

Figure 1:
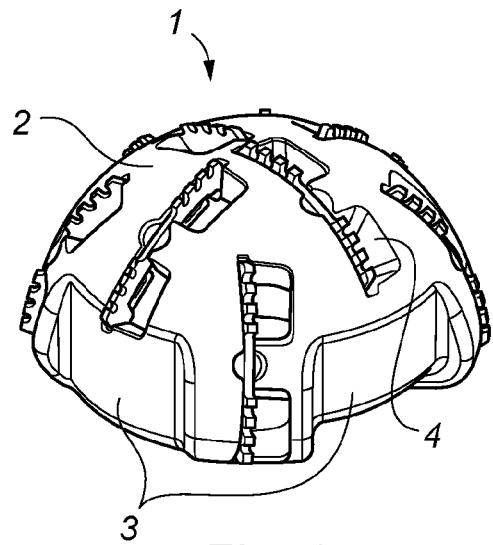

(52) U.S. Cl.
CPC ........ *A61B 17/8863* (2013.01); *A61B 17/162* (2013.01); *A61B 17/1624* (2013.01); *A61B 2017/00526* (2013.01); *A61B 2017/1602* (2013.01)

(58) Field of Classification Search
USPC ..................................................... 606/81, 80
See application file for complete search history.

(56) References Cited

U.S. PATENT DOCUMENTS

| | | |
|---|---|---|
| 2008/0215159 A1 | 9/2008 | Stamp |
| 2011/0184419 A1* | 7/2011 | Meridew ............ A61B 17/1746 606/80 |
| 2011/0202060 A1 | 8/2011 | White et al. |
| 2012/0191098 A1* | 7/2012 | Victor ................ A61B 17/1666 606/81 |
| 2012/0191099 A1* | 7/2012 | Victor ................ A61B 17/1666 606/81 |

FOREIGN PATENT DOCUMENTS

| | | |
|---|---|---|
| CN | 202036302 | 11/2011 |
| CN | 204733224 | 10/2015 |
| CN | 108472046 | 8/2018 |
| DE | 102014203456 | 9/2015 |
| EP | 2359755 | 8/2011 |
| EP | 2478852 | 7/2012 |
| EP | 3370627 | 9/2018 |
| IN | 201817017310 | 8/2018 |
| JP | 2015508009 | 3/2015 |
| WO | 2004/032767 | 4/2004 |
| WO | 2013126416 | 8/2013 |
| WO | 2017077340 | 5/2017 |

OTHER PUBLICATIONS

"European Application Serial No. 16794013.9, Response filed Jan. 16, 2019 to Communication pursuant to Rules 161(2) and 162 EPC dated Jul. 6, 2018", 10 pgs.
UK Intellectual Property Office, Search Report for GB1519624.9 dated Apr. 19, 2016, 2 pages.
International Searching Authority, International Search Report and Written Opinion for PCT/GB2016/053474 dated Apr. 13, 2017, 15 pages.
"European Application Serial No. 16794013.9, Communication Pursuant to Article 94(3) EPC dated Oct. 31, 2019", 4 pgs.
"European Application Serial No. 16794013.9, Response filed Mar. 12, 2020 to Communication Pursuant to Article 94(3) EPC dated Oct. 31, 2019", 20 pgs.
"Chinese Application Serial No. 201680076605.6, Office Action dated Jun. 2, 2020", (W/ English Translation), 10 pgs.
"Australian Application Serial No. 2016348912, First Examination Report dated Sep. 12, 2020", 5 pages.
"Chinese Application Serial No. 2016800766056, Response filed Oct. 19, 2020 to Office Action dated Jun. 2, 2020", with English claims, 13 pages.
"Japanese Application Serial No. 2018-543462, Notification of Reasons for Refusal dated Nov. 10, 2020", with English translation, 8 pages.
"Chinese Application Serial No. 201680076605.6, Office Action dated Mar. 2, 2021", with English translation, 14 pages.
"Indian Application Serial No. 201817017310, First Examination Report dated Mar. 12, 2021", with English translation, 5 pages.
"Chinese Application Serial No. 201680076605.6, Respone filed Apr. 30, 2021 to Office Action dated Mar. 2, 2021", with English claims, 19 pages.
"Japanese Application Serial No. 2018-543462, Examiners Decision of Final Refusal dated Jun. 8, 2021", with English translation, 4 pages.

* cited by examiner

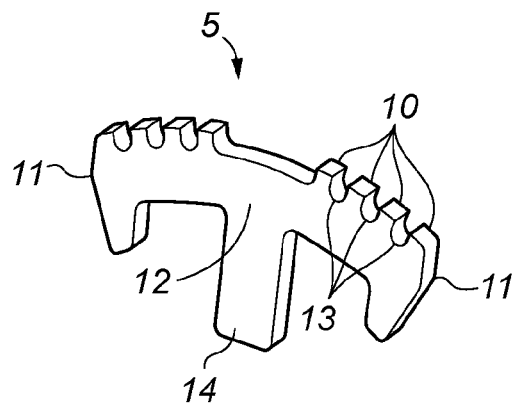 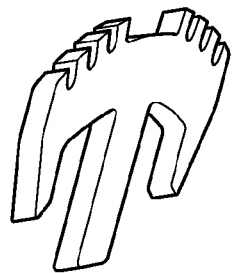
Fig. 5    Fig. 6
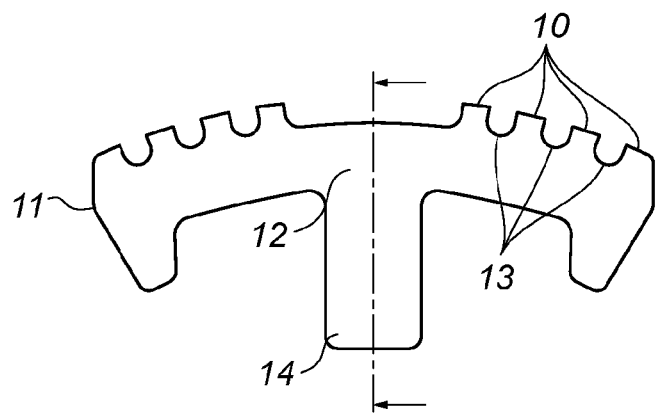 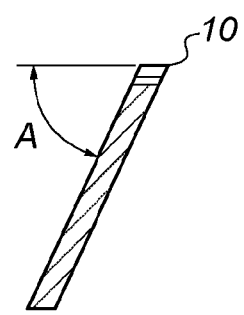
Fig. 7    Fig. 8

ROTARY CUTTER FOR PREPARING THE ACETABULAR SOCKET FOR A HIP IMPLANT

BACKGROUND

In order to place a hip cup implant in a patient's acetabular cavity, the surgeon must first prepare the patient's acetabular cavity to accept the implant. Generally, this portion of a hip arthroplasty is accomplished by use of acetabular reamers to enlarge and reshape or otherwise prepare the acetabular cavity of the patient. Prior art acetabular reamers generally include a hemispherical head having a cutting surface with a plurality of cutting edges. Such instruments are usually available in a variety of sizes. The surgeon must choose appropriate size or sizes of reamer for use during the surgery. In the case of porous coated (cement free) cup implants, a small interference fit is required between the implant and reamed acetabular socket so that the cup implant is a tight fit until bone ingrowth into the porous surface occurs to further strengthen fixation. If there is no interference or too little interference the cup implant may not be stable enough initially and the implant could fail. If there is too much interference the cup implant will be very difficult to fit. Therefore acetabular reamers must cut a precise enough cavity in the bone to achieve this small interference fit.

Acetabular reamers are expensive to manufacture due to their complexity and the need for sharp cutting teeth which are typically formed in several stages of manufacture. Furthermore a set of reamers includes many size variants corresponding to the cup implant size range so they take up a lot of space in the operating theatre. The majority of existing acetabular reamers are reusable so they must be cleaned and sterilised before use and between each use. Cleaning can take several days, therefore if a hospital has only a small number of acetabular reamers this can reduce the rate at which patients can be treated as the surgeon must wait for the reamer to be returned from cleaning before the next patient can be treated. In general reusable instruments bring an increased risk of infection to the patient as there is a chance they will not be cleaned thoroughly enough or sterilised correctly. Instruments with bone cutting functions become heavily contaminated with bone and tissue debris in use and are particularly difficult to clean. Furthermore after repeated reuse reamers become blunt and lose accuracy as the sharp cutting edges are worn down in use or due to attrition with other metal surfaces during the cleaning process.

STATEMENT OF INVENTION

To overcome these difficulties, the present invention proposes a single use acetabular reamer with a plurality of blades mounted in a plastic holder and releasable attachment means to a rotary driver.

DESCRIPTION AND ADVANTAGES

In one embodiment of the invention there is provided a rotary cutter with hemispherical shaped head and a plurality of blades mounted in said head, wherein each of said blades has securement means for securing each blade in position in said head by interacting with an inner surface of said head.

Preferably the securement means on said blades is a projection (e.g. a tab) which extends away from the cutting face of the blade and to the inside of the head when the blade is mounted on the head.

In order to fix the blade to the head, the projection can be bent over to secure said blades in position. This fixing process will be explained in more detail below.

While it may be the case that the hemispherical head can be made of multiple parts that are combined together to form the head, in preferred embodiments of the invention the head is formed as a single unit.

In another aspect, there is provided a two part rotary cutter comprising a first part being a hemispherical shaped head formed as a single unit and a second part comprising a plurality of cutting blades separable from said first part, wherein said plurality of cutting blades are mounted in said first part and secured in place by interaction with said first part.

It will be appreciated that the head should be formed with apertures to receive the plurality of blades. The blades will be placed within the apertures during manufacture of the final cutter and fixed into place.

In order to collect any bone fragments during the cutting procedure, typically at least one of said apertures will further comprise at least one circumferentially extending portion. Preferably, although not always necessarily, these circumferentially extending portions will extend through to the hollow of the hemispherical head. Furthermore, these portions will typically extend away from the direction of rotation.

In preferred aspects of the invention, the blade-receiving apertures will comprise projections which are designed to interact with a surface of a cutting blade when it is mounted in the aperture. These projections can act as stops in order to prevent the blade from being pushed too far into the head. Another useful feature of these projections is that they can be designed to be crushable. This is useful during the process of securing the blade into the head, where the head with mounted blades is clamped into a concave block. The block is profiled to give highly accurate positioning of the blades when the head is secured to the block, and the crushable projections allow slight realignment of the blades during the clamping of the head to the block in order to achieve accurate and desired alignment.

Although the head is described herein as being hemispherical, it need not follow a precise hemispherical configuration. For example, it is often useful for the head to be profiled around the region of the rim (and often extending somewhat into the hemisphere) to contain at least one cutaway portion (preferably 2, 3 or 4, preferably 4). This allows the surgeon visibility of regions of the tissue that is being cut, in particular the rim of the acetabulum.

Preferably the head is made by additive or rapid prototype manufacture (for example, selective laser sintering or stereolithography). The material of the head can be any suitable material that allows the blades to be suitable mounted. However, it have been found that a plastics material, preferably nylon, is well suited.

In order that the blades can be fixed securely to the head, and also to provide a cavity to collect bone shavings/swarf during cutting, the inside of the hemispherical head is substantially hollow.

However, it is appreciated that in order to reduce the number of components and material used in the set-up of the rotary cutter, it is desirable to configure the head such that it can be driven by direct action on the head itself. To this end, in preferred embodiments of the invention the hemispherical head comprises a rearward surface which has an outer profile that is substantially flat.

The inner profile of said rearward surface is preferably such that it allows entry of a driving means into said hollow of said head. In order that the driving means can directly drive the head without additional components, the inner profile is such that when said driving means is rotated within the hollow head rotation is allowed to a certain point of the inside of the rearward surface. Then the inner surface has a profile which acts as a stop to further rotation, such that further movement of the driving means on its own in that direction of rotation is restricted. Thus, when the driving means is further rotated in that direction, the driving means acts against the stop and thereafter rotates the whole head along with its own rotation.

Preferably the rotary cutter has releasable attachment means to a rotary driver which in turn has releasable attachment means to a surgical power drill.

The invention also provides a computer-readable medium having computer-executable instructions adapted to cause a 3D printer to print a hemispherical head of the invention.

Turning now to the blades, these are intended to be formed separately from the hemispherical head. Preferably they are cut from a metal sheet, for example by a laser cutting process. The metal may be e.g. stainless steel.

The blades may form a somewhat 'T'-like profile, with a cutting face forming the top of the 'T' and the projection which extends into the hemispherical head forming the leg of the 'T'. The cutting face may comprise a number of teeth or serrations. There may also be portions forming chip breaker slots, as discussed in more detail herein. The blades may also have ancillary projections at one or each arm of the blade which extend in the same direction as the primary projection. The ancillary projections may interact with portions in the blade-receiving apertures in the head in order to provide additional stability to the blade during mounting and/or cutting procedures.

The rotary cutter may have between 1 and 100 blades. In some case there may be 2, 3, 4, 5, 6, 7, 8, 9 or 10 blades. For example 8 blades.

The cutting blades in each sized reamer may be identical to one another. Alternatively, they may be of two or more different profiles.

Optionally, the multitude of blades in several or all sizes of reamers may be identical in profile.

As described in more detail herein, the blades can be mounted within said head at an angle, so that a cutting angle is established. In such scenarios, the blade receiving apertures in the head are therefore angled.

Furthermore in order to provide a clearance angle during cutting, the profile of the blade is also cut in manufacture (e.g. when laser cut) at an acute angle to the sheet surface. Therefore when each blade is mounted in the holder at an angle, both a cutting angle and clearance angle are established. At least the cutting edge should be cut at an acute angle as described, but it is preferable in the manufacturing process to cut around the entire profile at a constant angle, thus avoiding having to change the angle during the cutting process.

The present invention also provides a system for fixing a plurality of blades to a hemispherical shaped head, said system comprising:
(i) a hemispherical shaped head comprising a plurality of apertures;
(ii) a plurality of cutting blades, each of said blades having a projection extending away from a cutting face of said blade;
(iii) a concave hemispherical shaped block (designed to precisely set each blade in position relative to one another and relative to the plastic holder); and
(iv) means for bending each projection on said blade when said blade is mounted in an aperture on said hemispherical shaped head and said head with mounted blades is placed within said concave hemispherical block.

Preferably the means for bending each projection is a paddle, or any tool which is able to interact with the projection to bend it against the inside of the head.

In addition, it is preferable that the concave block has securement means associated with it such that when the hemispherical shaped head with mounted blades is placed within the block, the head is secured in place to prevent movement of said head during the bending of the projections of the blades. This securement means can be any appropriate structure known to the skilled person, such as a clamp or any clamp-like structure. In certain arrangements, the securement means is a clamp formed from bolting a collar over at least the rim of the hemispherical head.

The present invention also provides a method of manufacturing a rotary cutter as described herein, said method comprising:
(i) providing a hemispherical shaped head comprising a plurality of blade-receiving apertures;
(ii) mounting a cutting blade within at least one of said apertures, said blade having a projection extending away from a cutting face of said blade and into the hollow of said head; (iii) placing said hemispherical head with mounted blades in a concave hemispherical shaped block;
(iv) securing said hemispherical shaped head within said block; and
(v) inserting a paddle into said hollow of said hemispherical shaped head and rotating said paddle, wherein said paddle bends each projection on said blade against an inner surface of said head in order to secure the blade in position.

There is also provided a kit comprising:
(i) one or more rotary cutters as described herein;
(ii) a driver for connecting to one of said rotary cutters and a driving mechanism; and optionally
(iii) a gauge for checking an appropriate size of cut.

The rotary cutter may be of the same size, or there may be a range of different sizes of cutters.

SUPPLEMENTAL DESCRIPTION AND ADVANTAGES

The blades are made simply and cost effectively by cutting them out of a metal sheet preferably by laser cutting. Alternately the blades could be cut out of a metal sheet by water jet cutting or electrical discharge machining (EDM). The profile cut is angled so that the cutting edges have the appropriate geometry (cutting angle and clearance angle) for cutting bone when mounted in the holder. Preferably the entire profile of the blade is cut at the same angle as the cutting edges, however alternatively only the cutting edges are cut at an angle and the remaining portion is cut perpendicular to the faces. The blades include a portion extending to the inside of the plastic holder which is bent over to secure each blade in position. The plastic holder includes feature for releasable attachment to a rotary driver which in turn is attached to a surgical power drill. Preferably the plastic holder is manufactured in plastic by rapid prototype manufacture, for example selective laser sintering (SLS) or stereolithography (SLA).

In a preferred design the blades are positioned appropriately relative to one another such that in use, with the shaft held in one axial position, as the cutter completes one full revolution a full hemispherical portion of the bone socket surface is cut by the multitude of blades. Furthermore any serrations present on each tooth may be offset in relation to one another such that there is no possibility that there will be a circumferential region on the bone that is not cut appropriated due to it falling in the path of a gap caused by a serration.

Preferably the multitude of blades in each sized reamer are identical in profile. Alternatively the multitude of blades in each sized reamer could be of two or more different profiles. Alternatively the multitude of blades used in several sizes of reamers could be identical in profile. Alternatively the multitude of blades in all sizes of reamer could be identical in profile.

Preferably during assembly, the holder with blades inserted is clamped into a setting block with an accurately machined hemispherical bore. For example the setting block could be made from high carbon steel, with a ground hemispherical bore, to achieve a tolerance of plus or minus ten microns. As the clamping force is applied, crushable shoulder features in the plastic holder allows slight shift in the position of each blade so that the cutting portion of each blade is in full and intimate contact with the setting block surface. This sets each blade in a precise position relative to one another and relative to the holder, so that, as the portion of each blade extending to the inside of the plastic holder is bent over by a rotating tool, the precise position is maintained and each blade is accurately set into the reamer once it is removed from the setting block. As a result of this setting operation and because each reamer is single use, a greater degree of cutting accuracy is expected compared to conventional reusable reamers, therefore the chances of reliable achieving the small interference fit required for the cup in the bone socket are expected to improve.

Furthermore, because in the preferred embodiment both the blades and holder are made by modern rapid manufacturing processes (for example laser cutting and additive manufacture) it is feasible to make one or more special sized or patient specific sized reamers which are in-between the whole standard sizes if judge by the surgeon to be beneficial in a preoperative plan (for example a diameter 45.5 mm reamer when only diameters 45 and 46 mm are currently available as standard).

INTRODUCTION TO DRAWINGS

Figure 2:
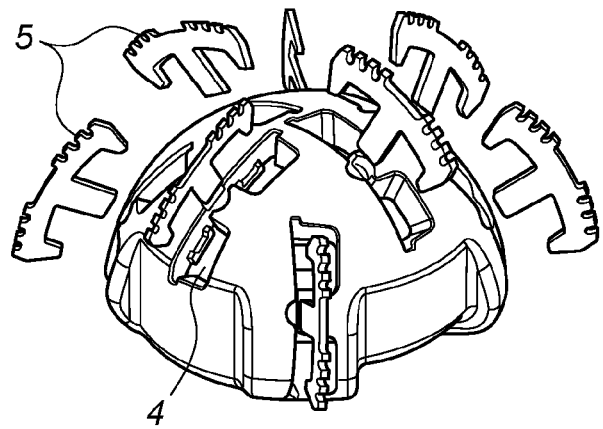
Figure 3:
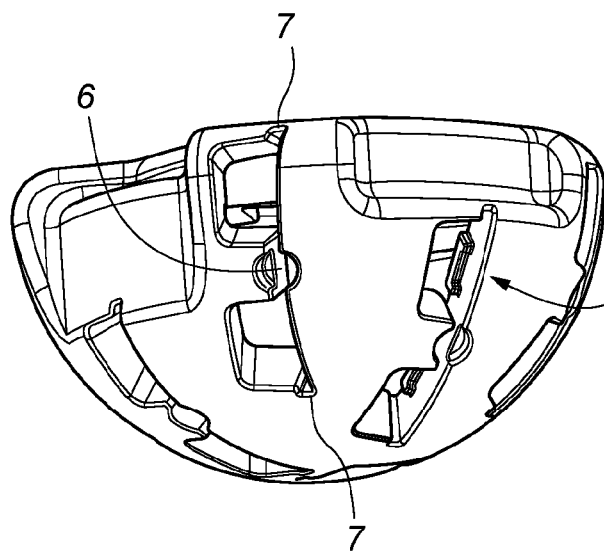
Figure 4:
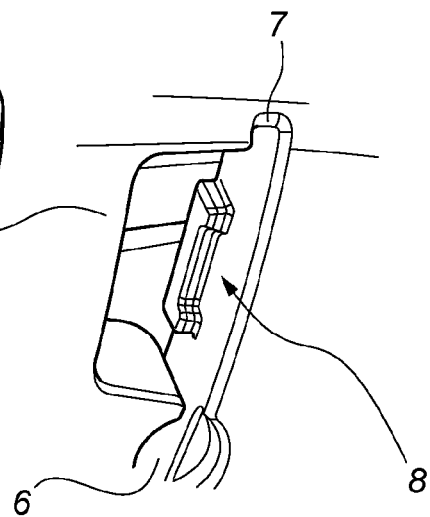
Figure 9:
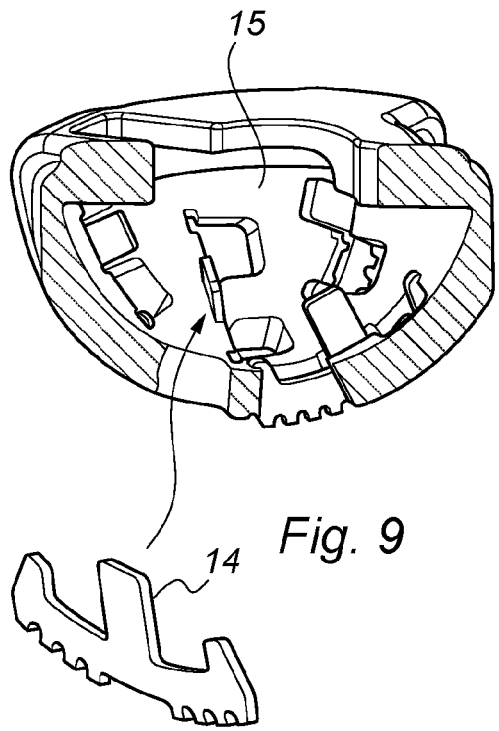
Figure 10:
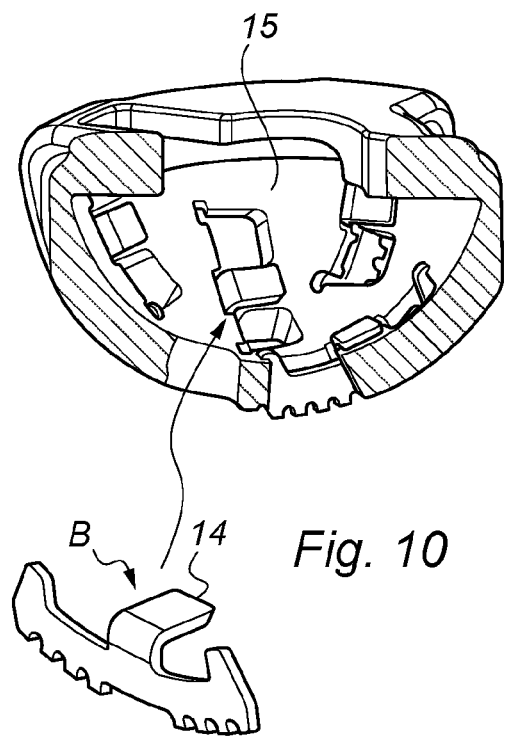
Figure 11:
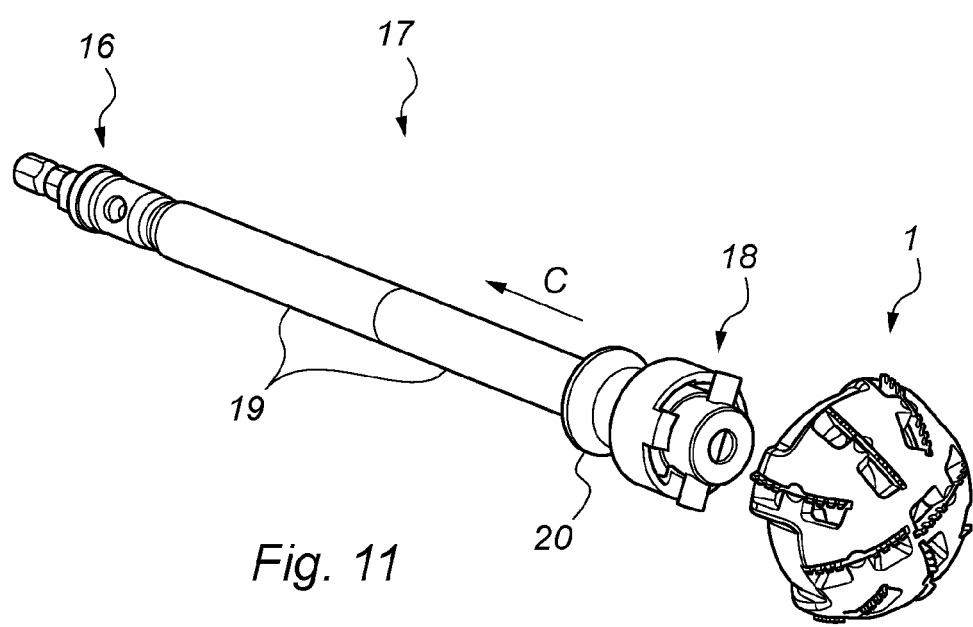
Figure 12:
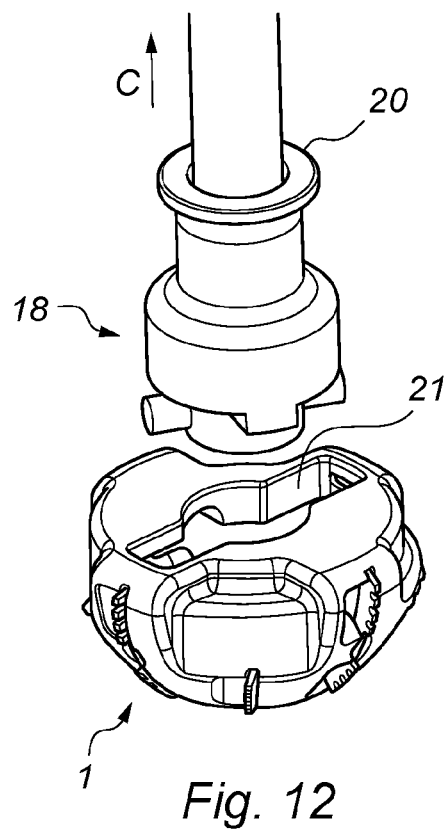
Figure 13:
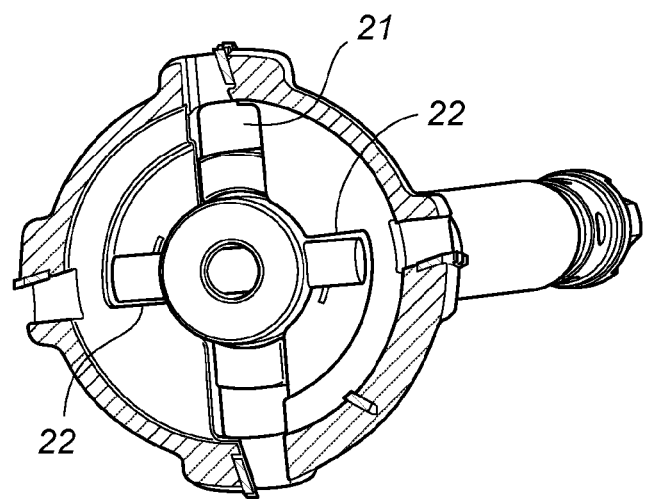
Figure 14:
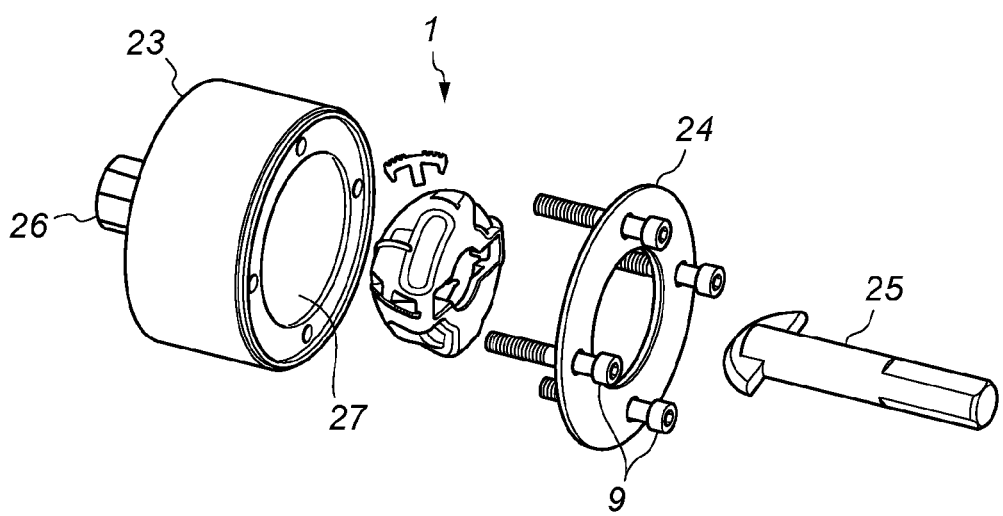
Figure 15:
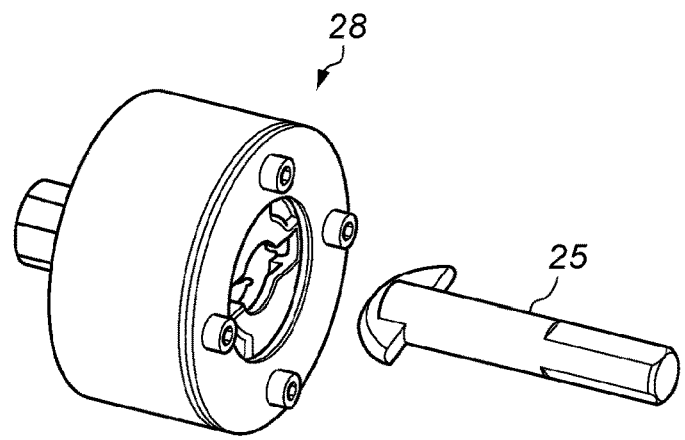
Figure 16:
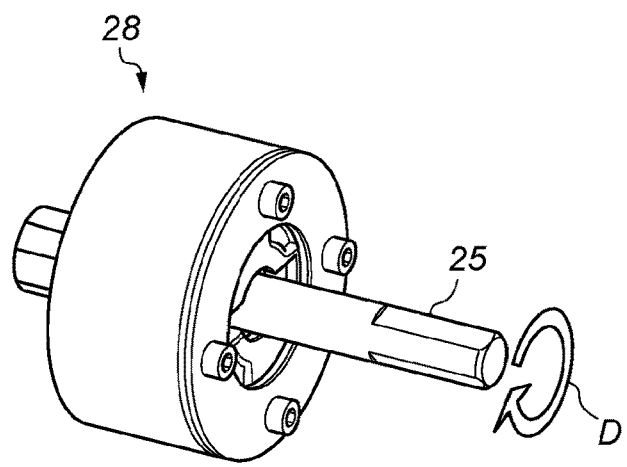
Figure 17:
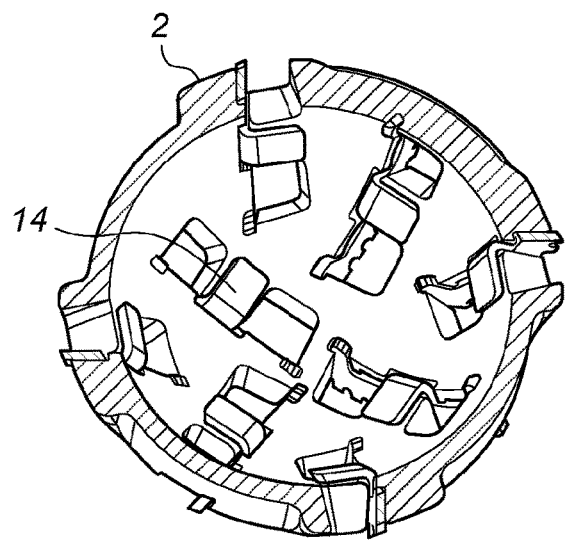

An example of the invention will now be described by referencing to the accompanying drawings:

FIG. 1 is a rotary cutter with blades assembled in position.
FIG. 2 is an exploded view of FIG. 1.
FIG. 3 is a pre-assembled plastic holder.
FIG. 4 is a close up view of a portion of the pre-assembled plastic holder of FIG. 3.
FIG. 5 is a metal blade.
FIG. 6 is an alternative view of the metal blade of FIG. 5.
FIG. 7 is view of the metal blade orientated in a plane perpendicular to the cut profile.
FIG. 8 is a cross sectioned view of FIG. 7.
FIG. 9 is a cross sectioned view of the assembled rotary cutter with blades inserted but before the portions extending to the inside of the holder are bent round. Inset to FIG. 9 is an isolated view of a pre-bent blade.
FIG. 10 is a cross sectioned view of the assembled rotary cutter with blades inserted and the portions extending to the inside of the holder bent round. Inset to FIG. 10 is an isolated view of a bent blade.
FIG. 11 is the assembled rotary cutter with rotary driver about to be connected.
FIG. 12 is an alternative view of the rotary cutter with rotary driver about to be connected.
FIG. 13 is a cross sectioned view of the rotary cutter with rotary driver connected via a bayonet feature.
FIG. 14 is an exploded view of the rotary cutter with manufacturing fixture for setting and securing the blades in position.
FIG. 15 is a view of the assembled manufacturing fixture with a separate rotating tool for bending over the portion of the blades extending to the inside of the holder.
FIG. 16 is view of the assembled manufacturing fixture with the separate rotating tool inserted (the arrow indicates rotation direction).
FIG. 17 is a cross sectioned view of the assembled rotary cutter with blades inserted and the portions extending to the inside of the holder bent over.

DESCRIPTION WITH REFERENCE TO DRAWINGS

In FIGS. 1 and 2 the anatomy of the rotary cutter (1) can be described as a plurality of blades (5) mounted in a hollow hemispherical shaped holder (2) with apertures (4) for capture and collection of bone cuttings (not shown). The holder includes several cutaway portions (3) to provide visibility to the rim of the acetabulum (not shown). FIGS. 3 and 4 show the isolated holder with receiving central slot (6) and side slots (7) for the blade and crushable shoulder features (8) to provide slight adjustment in blade position when clamped into the assembly fixture (28) shown in later figures. FIGS. 5-8 show the isolated blade (5) with cutting edges (10) and chip breaker slots (13) in-between. Said chip breaker slots help to break up the bone cuttings into smaller pieces for more efficient capture and passage into the hollow portion of the holder (15) via the apertures (4). The blades have middle portion (12) for engagement into the receiving central slot (6) of the holder (2) and side portions (11) for engagement into the receiving side slots (7) of the holder (2). It can be seen from FIGS. 7 and 8 that the blade profile is cut on an angle (angle A) so that the cutting edges (10) have the appropriate geometry (cutting angle and clearance angle) for cutting bone when mounted in the holder (2). In FIGS. 9 and 10 it can be seen that the portion of the blade extending to the inside of the holder (14) is bent over to secure the blades in position as indicated by arrow B and as will be described in later figures. FIGS. 11-13 show a rotary driver (17) for releasable attachment to the rotary cutter via a bayonet fitting end (18) and opposite end (16) with a standard drive for releasable attachment to a surgical power drill (not shown). Furthermore the rotary driver has a locking collar (20) to prevent accidental disengagement from the rotary cutter in use and a two-part holding sleeve (19) so that the shaft may be grasped safely to guide it, even when the shaft is rotated in the surgical power drill (not shown).

In use, the rotary driver (17) is first mounted in a surgical power drill (not shown) via a quick release standard drive fitting (16). The surgeon then selects the size of rotary cutter to start the reaming process and mounts it on the rotary driver by engaging a bayonet fitting (18 and 22). The bayonet fitting has a spring loaded locking collar (20) which locks automatically as the bayonet is rotated on assembly but requires manually pulling back in the direction of arrow (C) to allow rotation in the opposite direction for demounting the rotary cutter. The rotary cutter with rotary shaft and drill attached can then be offered up to the acetabular socket (not shown) for reaming of the bone. Often the surgeon will use a succession of rotary cutters of increasing sizes to prepare the acetabular socket for a specific sized cup implant, therefore the bayonet fitting is engaged and disengaged several times to change rotary cutter size in one operation. During reaming the surgeon may bias the rotary cutter to re-establish the natural position of the acetabular socket which may have migrated slightly due to the onset of arthritic disease. This is possible as the rotary driver has a two-part holding sleeve (19) for grasping and biasing it safely whilst rotating.

FIGS. 14-16 show the manufacturing fixture (28) for completing the assembly of the plurality of blades in the holder. Setting block (23) has an accurately machined hemispherical bore (27) and a spigot (26) for mounting the setting block in a fixed or rotatable spindle (not shown). The rotary cutter (1) with blades (5) inserted is clamped into the setting block by assembling a face plate (24) to the block (23) and tightening a multitude of screws (9) so that the face plate tightens against the flat face of the rotary cutter. As the clamping force is applied, crushable shoulder features (8) in the blade recesses of the plastic holder (2) allow slight shift in the position of each blade so that the cutting portion of each blade (10) is in full and intimate contact with the setting block bore surface (27). This process sets each blade in a precise position relative to one another and relative to the holder. In FIGS. 14 and 15, it can be seen that a rotating tool (25) is inserted into the bayonet slot (21) of the rotary cutter in axial alignment with the setting block. The rotary tool is attached to a fixed or rotatable spindle (not shown), so that as either the setting fixture (28) or the rotary tool (25) is rotated through a full revolution (as indicated by arrow (D), the portions of each blade extending to the inside of the plastic holder are bent over by the rotary tool to secure the blades. Furthermore due to the setting fixture and setting operation, the precise position of each blade is maintained once the rotary cutter is removed from the manufacturing fixture.

The invention claimed is:

1. A rotary cutter comprising:
a hemispherical shaped head including an outer surface and an inner surface; and
a plurality of blades mounted in said head, wherein each of said blades has a body portion disposed within one of a plurality of enclosed blade receiving slots formed in said head, one or more cutting edges extending from a superior side of said body portion and beyond said outer surface of said head, and a fastener extending from an opposing inferior side of said body portion for securing said blade in position in said head by interacting with said inner surface of said head, said fastener on each of said blades comprising a projection that extends through said blade receiving slot to an inside of said head, wherein said projection is bent within said head at an angle relative to said body portion and engages said inner surface of said head.

2. The rotary cutter of claim 1, wherein said head is formed as a single unit.

3. The rotary cutter of claim 1, wherein at least one of said blade receiving slots comprises at least one circumferentially extending portion.

4. The rotary cutter of claim 1, wherein at least one of said blade receiving slots comprises projections which interact with a surface of a blade of the plurality of blades.

5. The rotary cutter of claim 1, wherein said head comprises at least one cutaway portion extending along a rim of the head.

6. The rotary cutter of claim 1, wherein the head is made by additive or rapid prototype manufacture.

7. The rotary cutter of claim 6, wherein the head comprises a plastics material.

8. The rotary cutter of claim 1, wherein an inside of the hemispherical shaped head is hollow.

9. The rotary cutter of claim 1, wherein the hemispherical shaped head comprises a rearward surface which has an outward profile that is substantially flat.

10. The rotary cutter of claim 9, wherein said rearward surface comprises a slot to allow entry of a rotatory tool into a hollow of said head, and wherein an inner profile of the hollow head comprises a rotation stop to restrict independent rotation of the rotary tool relative to the head.

11. The rotary cutter of claim 1, wherein the plurality of blades is between 1 and 100 blades.

12. A two part rotary cutter comprising:
a first part being a hemispherical shaped head formed as a single unit and including an outer surface and an inner surface; and
a second part comprising a plurality of generally T-shaped cutting blades separable from said first part, said plurality of cutting blades mounted in said first part and secured in place by interaction with said first part, wherein each of said cutting blades includes a body portion disposed within one of a plurality of blade receiving slots formed in said first part, one or more cutting edges extending from a superior side of said body portion and beyond said outer surface of said first part, and a projection extending from an opposing inferior side of said body portion and through said blade receiving slot to an inside of said first part, and wherein said projection is bent within said first part at an angle relative to said body portion and engages said inner surface of said first part.

13. A rotary cutter comprising:
a hemispherical shaped head including an outer surface and an inner surface; and
a plurality of generally T-shaped blades mounted in said head, wherein each of said blades has a body portion disposed within one of a plurality of blade receiving slots formed in said head, one or more cutting edges extending from a superior side of said body portion and beyond said outer surface of said head, and a fastener extending from an opposing inferior side of said body portion for securing said blade in position in said head by interacting with said inner surface of said head, said fastener on each of said blades comprising a projection that extends through said blade receiving slot to an inside of said head, wherein said projection is bent within said head at an angle relative to said body portion and engages said inner surface of said head.

* * * * *